United States Patent [19]

McNeil

[11] Patent Number: 4,551,141
[45] Date of Patent: Nov. 5, 1985

[54] METHOD AND APPARATUS FOR REMOVING LIQUIDS FROM A DRAINAGE DEVICE

[75] Inventor: Charles B. McNeil, Edina, Minn.

[73] Assignee: Surgidyne Inc., Buford, Ga.

[21] Appl. No.: 519,723

[22] Filed: Aug. 2, 1983

[51] Int. Cl.$^4$ .............................................. A61M 1/00
[52] U.S. Cl. ..................................... 604/317; 604/319
[58] Field of Search ................................. 604/317–329, 604/73, 74, 75, 49, 51, 54; 285/334.4, 331; 141/59; 137/205; 128/760, 767

[56] References Cited

U.S. PATENT DOCUMENTS

| | | | |
|---|---|---|---|
| 3,424,218 | 1/1969 | Vanderbur, Jr. et al. | 604/408 |
| 4,084,593 | 4/1978 | Järund | 604/73 |
| 4,126,167 | 11/1978 | Smith et al. | 604/317 |
| 4,265,243 | 5/1981 | Taylor | 128/760 |
| 4,319,573 | 3/1982 | Whitlock | 604/323 |
| 4,435,171 | 3/1984 | Goldberg et al. | 604/317 |
| 4,443,219 | 4/1984 | Meisch et al. | 604/323 |

*Primary Examiner*—C. Fred Rosenbaum
*Assistant Examiner*—J. L. Kruter
*Attorney, Agent, or Firm*—Larson and Taylor

[57] ABSTRACT

A closed system method and apparatus for removing collected liquid from a portable closed wound suction drainage device which reduces the potential contamination of the drainage device and cross infection from the use of the drainage device is disclosed. A disposable collection bag is attached to the outlet (emptying port) of the drainage device and the contents are transferred in a closed system procedure into this collection bag through a one-way inlet. After transferring the contents, the filled collection bag is removed from the outlet and capped for subsequent disposal, and a new collection bag is attached to the outlet of the drainage device. Preferably, the collection bag is compacted, such as by rolling, and held in this compact form by a retainer. A protective closure cap is provided for the inlet of the collection bag to form a cover and seal for the inlet both before fitment to the device and after filling. The cap also prevents leakage or the escape of contamination from the disposable collection bag after filling. A special skirt is provided with the bag inlet connector to prevent contamination of the inlet during the attachment procedure and to form a protective seal and cover over the exterior of the drainage device outlet to prevent contamination of the outlet while the device is collecting the drainage. The skirt also combines with the tapered inlet to provide a secure and leakfree fitment between collection bag and drainage device.

12 Claims, 6 Drawing Figures

METHOD AND APPARATUS FOR REMOVING LIQUIDS FROM A DRAINAGE DEVICE

FIELD OF THE INVENTION

The present invention relates generally to a portable, single patient use, closed wound suction drainage device, and more particularly to a closed wound suction drainage device which is periodically emptied while remaining connected to the patient's wound site, and which is usable for an extended period of time without contamination.

BACKGROUND OF THE INVENTION

The use of portable, single patient use, closed wound suction devices to drain surgical wounds is increasing in surgical practice. The closed wound suction device includes a suction inducing reservoir where the suction is applied to the patient's surgical wound via a connector tubing with a distal tip placed in the wound site to be drained. An air tight seal is created at the point the tubing exits through the skin to provide a "closed wound" so that suction drainage is effective in removing wound exudate and other unwanted material from the wound site. Sometimes the wounds are contaminated and sometimes the wounds are clean and uncontaminated. The reservoir collects the exudate sucked from the wound via the tubing until the reservoir is ready to be emptied, or until such time or at such time intervals as directed by the physician. The container reservoir generally fills in a matter of hours and is then emptied. When the reservoir does not fill quickly, the reservoir is usually emptied at least once every twenty-four hours. After emptying with the suction off, the suction device is reactivated for further collection.

During the filling cycle time interval, and over the extended period of time the device is used, the bacterial count in reservoirs collecting drainage from contaminated wounds increase exponentially as the liquid in the reservoir is a superior bacteria culture medium. In clean, uncontaminated wounds, the reservoir usually becomes contaminated with exogenous bacteria within twenty-four to forty-eight hours due to the repeated opening of the reservoir during emptying. So in either type of wound, the suction drainage collection reservoir becomes a harbor for bacteria as these devices are normally in use for three to five days or longer.

In order to empty the liquid from the closed wound suction drainage device, the collection reservoir is opened, usually by removing a male plug from a female outlet (emptying port) of the reservoir. The contents are then emptied into an open basin or open graduated container. From there, the liquid is transferred to a disposal site such as a toilet or "hopper" (a special flushable sink-like unit). In order to empty the drainage device it is common practice, and with some devices it is essential, to squeeze or compress the device to create a positive pressure in the drainage device to expel the liquid through the outlet. When the contents are so expelled, the drained liquid may be aerosoled due to the rapid expulsion and splashing in the collection receptacle. In addition, even when emptying a reservoir by gravity flow, some splashing of the liquid is almost inevitable. Shaking of the device is also often required to completely empty it as residual pools of exudate are common to collection reservoirs, especially in certain spring activated and balloon type devices. It is important to completely empty the devices as physicians determine the status of the draining wound by the volume of exudate collected over time. In either event, the aerosol or spilled exudate are often heavily laden with bacteria and are obvious sources of nosocomial infection. The bacteria can infect the patient, the person emptying the drainage device as well as other patients or persons in close proximity that may be exposed to the bacteria contained in the aerosol or spilled exudate.

The transmission of hospital infection by aerosol effects is well documented in the medical literature. In order to prevent or reduce aerosol induced cross infection from wall suction systems, hospitals have used bacterial filters on suction collection canisters. Further, other forms of disposable suction collection receptacles are usually considered to be "contaminated waste" and are handled according to special procedures established for handling and disposing of such materials. Portable closed wound suction units have been a necessary exception to the practices followed for the other suction collection devices as they are attached to the patient, and no closed method of handling the waste has been available.

Each time that a drainage device is opened to drain the liquid therefrom, there is also an increased risk of contamination from the outside environment reaching the inside of the drainage device. When the reservoir of the drainage device is contaminated with an outside contanimant, there is a danger of retrograde infection of the patient's wound. Obviously, the more times the drainage device is opened, the greater the danger of inadvertently contaminating the drainage reservoir; and the longer the device is used and the drains are left in place, the greater the possibility of retrograde infection of the patient's wound from outside contaminants. Some surgeons routinely remove the drainage system after three days time even though drainage has not fully ceased due to their fear of retrograde infection of the wound from the ouside contaminants.

There has been disclosed in the prior art systems for collecting liquids from a patient in a first container, and subsequently transferring these liquids to a flexible second container. Examples of devices such as these which are used to collect urine from the bladder of a patient are disclosed in U.S. Pat. No. 3,888,126 (Cross) and U.S. Pat. No. 4,319,573 (Whitlock). The use of flexible collection containers and the like have also been disclosed in the following U.S. patents: U.S. Pat. No. 4,334,537 (Peterson); U.S. Pat. No. 3,312,221 (Overment); U.S. Pat. No. 3,724,461 (Eisenberg); and U.S. Pat. No. 3,926,233 (Brendling).

SUMMARY OF THE INVENTION

In accordance with the present invention, a method and apparatus for removing collected liquid from a portable closed wound suction drainage device which reduces contamination of the drainage device and cross infection from the use of the drainage device is provided. The portable closed wound suction drainage device typically includes a collection chamber, a suction means for creating a negative pressure in the collection chamber, an inlet for the collection chamber which is connected to the surgical drain(s) placed in the wound site of the patient to be drained, and an outlet for emptying the collection chamber as necessary. When the collection chamber requires emptying, it is necessary to remove the liquid therefrom so that the drainage device can be reactivated and reused for additional drainage collection. In order to empty the device while maintaining a closed system during the emptying procedure, a collapsed and disposable collection bag having a one-way valved inlet is used. The valved inlet of the collection bag is attached to the outlet of the collection chamber. When the drainage device requires emptying, the liquid in the collection chamber is transferred into the collection bag. The collection bag is then disengaged from the outlet of the collection chamber and disposed of accordingly.

By use of the present invention, the liquid transferred from the collection chamber is never exposed to the surrounding environment so that there is no chance for infecting the person emptying the container as well as the patient or other patients or persons in close proximity. In addition, in the preferred embodiment of the present invention, a new collection bag is immediately connected to the outlet of the collection chamber as soon as the filled bag is removed. In this manner, contamination of the drainage device from the outside environment through the outlet is substantially eliminated.

In the preferred embodiment of the present invention, the collection bag further includes a closure cap which is attached to the collection bag. In addition, a skirt is provided around the inlet of the collection bag which helps to prevent contamination of the inlet which could be transferred to the outlet of the drainage device and thereafter to the collection chamber. The skirt also provides a protective cover over the exterior of the outlet of the collection reservoir to prevent contamination of the outlet by the outside environment while the device is being used to collect drainage, which contamination could then be transferred to the collecton reservoir and cause retrograde infection. Preferably, the closure cap contacts the skirt when the cap is engaged on the inlet to provide a seal around the inlet prior to use.

For convenience and optimal performance, the collection bag is preferably compacted, such as by rolling, to provide a small, easily stored and used collection bag. The compact form embodiment is most desirable while the bag is attached to the outlet of the collecton reservoir during the filling cycle (period) as it does not obtrude significantly or in a detrimental manner. In order to maintain the collection bag compacted, a suitable retainer is provided.

In order to transfer the liquid collected in the collection chamber from the drainage device, the suction means is preferably a resilient and collapsible pump means or balloon activated means which causes a positive pressure in the collection chamber to exist when the pump is forcibly activated or the balloon is collapsed. Therefore, when the suction pump is actuated, liquids in the collection chamber are expelled through the outlet and into the collection bag attached to the outlet. Conveniently, the collection bag is made of transparent, or semi-tranpasrent materials on at least one side which includes calibrations thereon so that the amount of liquids collected in the collection chamber can be measured.

Other features and advantages of the present invention are stated in or apparent from a detailed description of the presently preferred embodiment of the invention found hereinbelow.

DETAILED DESCRIPTION OF THE PREFERRED EMBODIMENT

Figure 1:
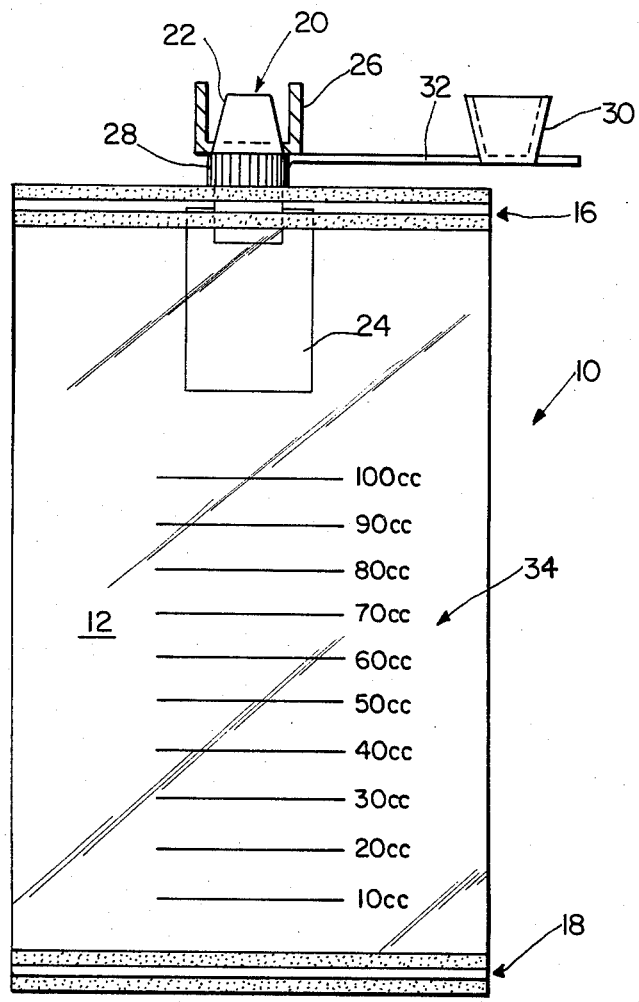
FIG. 1 is a front elevation view of a collection bag according to the present invention.

With reference now to the drawings in which like numerals represent like elements throughout the several views, a presently preferred embodiment of a collection bag 10 is depicted in detail in FIG. 1. Collection bag 10 includes a front wall 12 and a rear wall 14 with at least one wall formed of transparent or semi-transparent plastic material, such as PVC, polyethylene, or the like. Conveniently, front wall 12 and rear wall 14 are formed from a sleeve of material which is pressed flat and provided with a top seal 16 and a bottom seal 18. Alternatively, walls 12 and 14 are formed from two sheets of plastic film and sealed on all outside edges.

Extending through top seal 16 between front wall 12 and rear wall 14 is a tubular inlet 20. At the upper end, inlet 20 is provided with a tapered nose 22 which is adapted to be received in various sized tubings, outlets, or fittings. At the lower end, a one-way inlet valve 24 is attached to inlet 20. Inlet valve 24 can be a flutter valve, flap valve, umbrella valve, or other suitable valve for preventing reverse flow through inlet 20 while allowing flow readily into collection bag 10.

Figure 2:
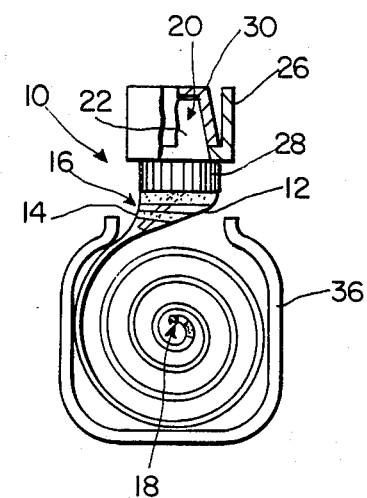
FIG. 2 is a side elevation view of the collection bag depicted in FIG. 1 in a compact form.

Located around tapered nose 22 is an upstanding circular skirt 26. Skirt 26 is attached to tubular inlet 20, and is conveniently integrally molded therewith. Located beneath skirt 26 is a collar 28 to which a cap 30 is attached by a flexible tether 32. As shown in FIG. 2, cap 30 is resiliently received on tapered nose 22 and contacts skirt 26 to provide a complete seal about tapered nose 22.

Preferably, collection bag 10 is provided with calibration marks 34 on front wall 12 which wall is transparent or semi-transparent. These calibration marks 34 are used to indicate the amount of liquid which is collected in collection bag 10. The amount of liquid collected is easily seen through transparent front wall 12.

As shown in FIG. 2, front wall 12 and rear wall 14 are conveniently rolled up so that collection bag 10 is provided in a compact and least obtrusive form for use during the fill cycle of the collection reservoir of the suction drainage device as well as for compactness in shipping and storage. In order to maintain collection bag 10 in compact form, a retainer such as a U-shaped bar 36 is provided. Other forms of retention means such as clips, ties, or bands are also suitable. The rolled up portion of collection bag 10 resiliently presses against the inside walls of U-shaped bar 36 to hold U-shaped bar 36 in place. However, the resilient pressure of collection bag 10 allows U-shaped bar 36 to be easily removed from collection bag 10 when collection bag 10 is to be filled.

Figure 3:
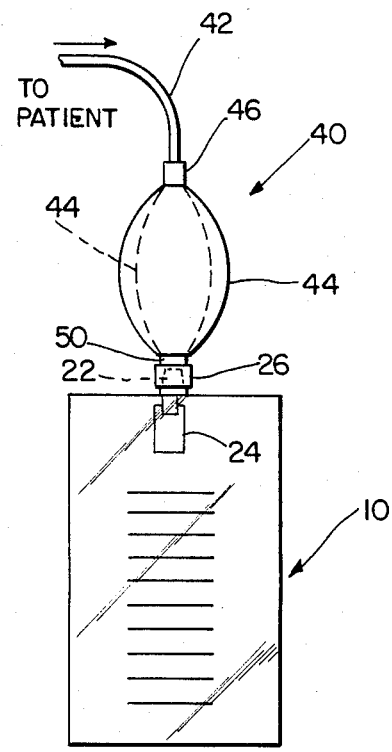
FIG. 3 is a schematic front elevation view of a drainage device with a collection bag attached according to the present invention.

Depicted in FIG. 3 is a drainage device 40 to which collection bag 10 is attached. Drainage device 40 is a closed wound suction drainage device of which many types are known in the prior art. Typically, drainage device 10 is connected to the site of the patient to be drained by a suitable tubing 42 which empties into a collection chamber or reservoir 44 through a one-way valve 46. At the lower end of reservoir 44 is an outlet 50 which is suitably sealed and which may also include a one-way valve.

In operation, drainage device 40 and collection bag 10 function in the following manner. Initially, after tubing 42 is connected to the site of the patient to be drained, reservoir 44, with outlet 50 open, is squeezed (shown by phantom lines) by a physician or attendant. After outlet 50 is sealed, reservoir 44 conveniently acts as a suction pump when physically collapsed as the elasticity of reservoir 44 causes it to seek to return to its original shape (shown by solid lines). As wound drainage liquid is withdrawn through tubing 42 into reservoir 44, reservoir 44 begins to expand. Reservoir 44 is designed to supply substantially constant negative pressure as it continues to seek to return to its original state throughout the filling cycle.

Figure 4:
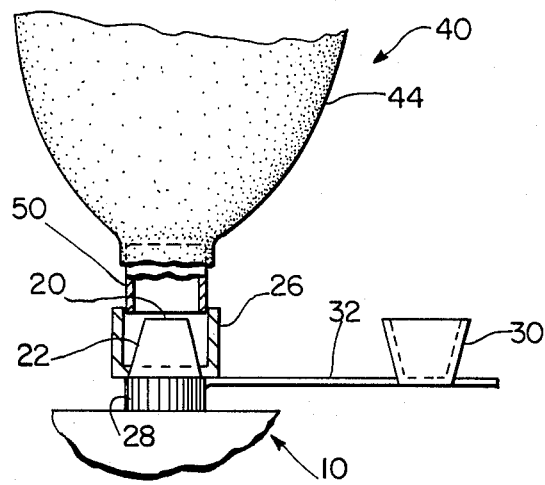
FIG. 4 is a front elevation view of the inlet connector of the collection bag and outlet of the collection device reservoir just prior to connection.
Figure 5:
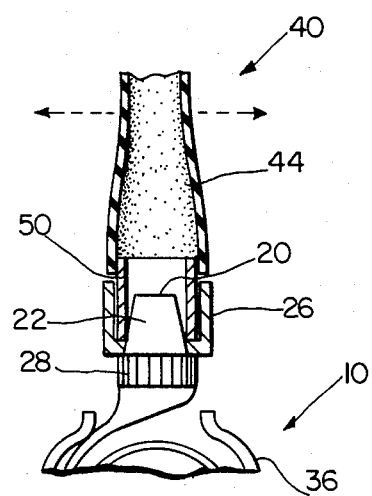
FIG. 5 is a side elevation view of the collection bag in compacted form attached to a collection reservoir in the compressed (activated) state.

Collection bag 10, in the compact form shown in FIG. 2 but with cap 30 removed from inlet 20 as shown in FIG. 4, is attached to outlet 50 of the suction collection reservoir 44 which is in the collapsed (activated state) in FIG. 5. It should be appreciated that collection bag 10 is initially sterile, being supplied in a sterile package with drainage device 40 or in a separate sterile package. As shown in FIGS. 4 and 5, tapered nose 22 is resiliently received in outlet 50. Tapered nose 22 forces outlet 50 against the interior surface of skirt 26. The interior surfaces of skirt 26 and the exterior surface of nose 22 mate with exterior and interior surfaces of outlet 50 to provide a protective cover over the exterior surfaces of outlet 50, and a leak free, secure friction fit between tapered nose 22 and outlet 50. The protective cover and seal provided by the skirt 26 prevents contamination of outlet 50 by the outside environment, and subsequent contamination of the collecton reservoir 44. The secure friction fit between collection bag inlet 20 and drainage device outlet 50 prevents leakage or accidental disconnection of collection bag 10 from drainage device 40.

According to the present invention, as soon as suction pump is activated by squeezing reservoir 44, collection bag 10 is attached to outlet 50 of drainage device 40. In this manner, the sterility of outlet 50 is best maintained even though collection bag 50 is not needed for emptying drainage device 40 at this time. In addition, any leakage from outlet 50 is also prevented. Initially, collection bag 10 is stored and provided for use in the compact form depicted in FIG. 2 where collection bag 10 is rolled up and retained by U-shaped bar 36. In addition, cap 30 has been retained on tapered nose 22 and contacts skirt 26 so that an airtight seal is provided around inlet 20 which has previously been and is thus still sterile.

In order to attach collection bag 10 to drainage device 40, cap 30 is removed fom tapered nose 22 and tapered nose 22 is resiliently received in outlet 50 so that skirt 26 surrounds the end of outlet 50 as well as shown in FIG. 5. In this manner, collection bag 10 is removably held on drainage device 40 and at the same time the end of outlet 50 is covered by skirt 26 and maintained in a relatively sterile, uncontaminated condition throughout the operation of drainage device 40. The compact form of collection bag 10 also helps to prevent an inadvertent bumping of collection bag 10 which would tend to disengage nose 22 from outlet 50.

When it is time to empty reservoir 44 after drainage device 40 has operated and has become filled or partially filled with liquid from the sites to be drained, drainage device 40 is emptied and reactivated for continued use. In order to empty drainage device 40, U-shaped bar 36 is removed from around the rolled portion of collection bag 10. Collection bag 10 can be unfurled manually or collection bag 10 will unfurl by itself as it fills with liquid. Reservoir 44 is then squeezed to expel the liquid contained therein through outlet 50 and into collection bag 10.

Due to the one-way nature of inlet valve 24, no liquid or gases generated by the transferring of the liquid from reservoir 44 into collection bag 10 escape to the surrounding environment. After drainage device 40 is emptied, or after collection bag 10 is full, collection bag 10 is removed from drainage device 40 by withdrawing tapered nose 22 from outlet 50. It should be noted that skirt 26 also helps prevent the attendant from accidentally contacting tapered nose 22 which has been exposed to the liquid, and skirt 26 can be safely held to help withdraw nose 22 from outlet 50.

Figure 6:
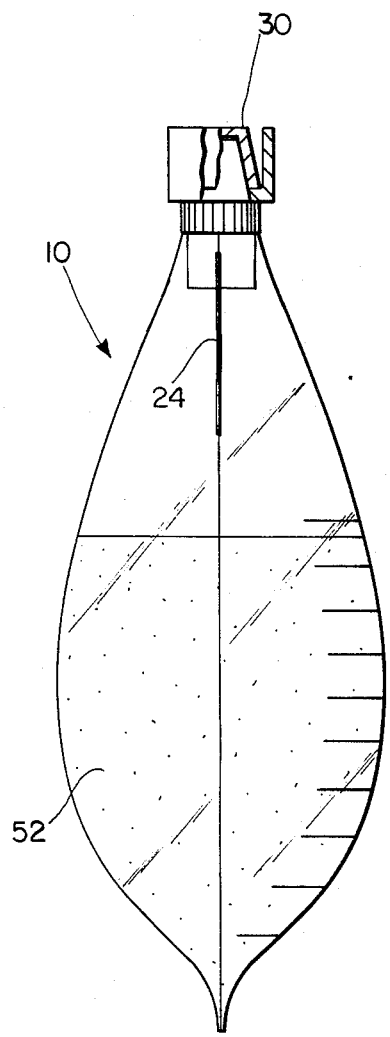
FIG. 6 is a side elevation view of the collection bag in the filled state ready for disposal.

As soon as collection bag 10 is removed from drainage device 40, cap 30 is replaced on tapered nose 22 as shown in FIG. 6. This insures that there is no escape of the residual liquid left within tapered nose 22 and above inlet valve 24 to the surrounding environment. Subsequently, if desired, the amount of liquid collected in collecton bag 10 is measured by calibration marks 34 on front wall 12. After that, collection bag 10 is suitably disposed of or, if desired, sent to a lab where studies on the liquid contained therein are made.

As soon as possible after filled collection bag 10 is removed from drainage 40 and capped, a new collection bag 10 is attached to valved outlet 50. It should be noted that the tapered nose 22 of the new collection bag 10 has been maintained in a sterile condition by skirt 26 and cap 30. Thus, by attaching a new collection bag 10 as soon as the filled collection bag is removed, the relative sterility or non-contamination of outlet 50 is maintained. Although it is not essential to attach a new collection bag 10 until drainage device 40 is filled again as long as outlet 50 is suitably sealed to prevent cross contamination to others, there is a danger of contaminating outlet 50 by exposure to the surrounding environment in the interim. This contamination might work its way back through outlet 50 during the next filling of a collection bag 10 and eventually work its way back to the site in the patient to be drained.

Although the present invention has been described in use with depicted drainage device 40, it should be appreciated that drainage device 40 is only exemplary of various closed wounds suction drainage devices which are commercially available. Typically, such drainage devices are portable and disposable, although used with the same patient for as long a time as drainage persists. In other portable drainage devices, the suction on the reservoir is induced by bellows, springs, balloons, elastic bulbs or other suitable means. Non-portable drainage devices using 110 volt A.C. to power a suction pump or using wall suction piped from a central source in a hospital are also suitably used with collection bag 10.

It should also be appreciated that the present invention is also usable with a rigid collection reservoir as opposed to the flexible collection reservoir disclosed. When a rigid collection reservoir is drained using a collection bag according to the present invention, an air vent must also be provided to relieve the negative pressure in the rigid collection reservoir caused by the draining. Such an air vent could be provided in the rigid collection reservoir itself, or in tapered nose 22 of collection bag 10 in a manner similar to some I.V. Administration sets which employ rigid containers.

Thus, while the present invention has been described with respect to an exemplary embodiment thereof, it will be understood by those of ordinary skill in the art that variations and modifications can be effected within the scope and spirit of the invention.

I claim:

1. A method for removing collected liquid from a portable closed wound suction drainage device which reduces contamination of the drainage device and cross infection from the use of the drainage device comprising the steps of;
    providing a catheter and collapsible suction reservoir having a one way valve at the inlet and having a single outlet,
    providing a rolled up collapsible collection bag having an inlet with a one way valve therein and retaining means to hold the bag in a rolled up condition,
    attaching the inlet of the collection bag to the outlet of the collapsible suction reservoir to provide fluid communication between the suction reservoir and the collection bag when the one way valve in the collection bag is open,
    removing the retainer means from the collapsed rolled up collection bag,
    collapsing the suction reservoir to close the one way valve at the inlet of the suction reservoir and to open the one way valve in the collection bag to force liquid from the suction reservoir into the collection bag,
    removing the filled collection bag and attaching another rolled up collapsible collection bag to the outlet of the suction reservoir and
    releasing the suction reservoir to create a suction within the reservoir and to open the one way valve at the inlet of the suction reservoir and to maintain the one way valve in the collection chamber closed.

2. A method for removing collected liquid from a suction drainage device as claimed in claim 1 wherein a closure cap is provided for the inlet of the collection bag, and further including the steps of removing the cap prior to attaching the inlet of the collection bag to the outlet of the collection chamber, and reapplying the cap to the inlet of the collection bag after the collection bag is disengaged from the outlet of the collection chamber.

3. A method for removing collected liquid from a suction drainage device as claimed in claim 2 wherein the inlet of the collection bag is received in the outlet of the collection chamber and a skirt is provided around the inlet of the collection bag to reduce contamination of the outer surface of the inlet of the collection bag and hence contamination of the drainage device and to reduce contamination of the outlet of the collection chamber and, hence, contamination of the drainage device.

4. A method for removing collected liquid from a suction drainage device as claimed in claim 3 wherein the skirt is contacted by the cap when the cap is attached around the inlet of the collection bag to provide a seal around the outer surface of the inlet of the collection bag to protect the inlet from contamination prior to use.

5. A method for removing collected liquid from a suction drainage device as claimed in claim 3 wherein the collection bag and the inlet of the collection bag are made of plastic materials, and the material of the front wall of the collection bag is transparent.

6. A method for removing collected liquid from a suction drainage device as claimed in claim 3 wherein the collection bag is provided with collected liquid calibrations and further including the step of measuring the amount of liquid collected in the collection bag after the collection bag is disengaged from the outlet of the collection chamber.

7. A closed wound drainage system for reducing contamination of a drainage site of a patient and cross contamination of others comprising,
    a collapsible suction reservoir having an inlet and outlet,
    a one way valve at the inlet of said collapsible suction reservoir,
    a catheter having one end attached to the inlet of said collapsible suction reservoir, the other end of said catheter being in fluid communication with the drainage site of a patient,
    a closed, collapsed and disposable collection bag having an inlet and including a one way valve therein and means for retaining said collection bag in a collapsed condition,
    the inlet of the collection bag being connected to the outlet of the suction reservoir and
    the suction reservoir including pump means whereby when said pump means increases the pressure within the suction reservoir the one way valve at the inlet of the suction reservoir is closed and the one way valve in the collection bag is opened to cause fluid collected in the reservoir from the patient's drainage site to pass from the reservoir into the collection bag after removal of the retaining means and when said pump means decreases the pressure within the suction reservoir the one way valve in the inlet of the suction reservoir is opened and the one way valve in the collection bag is closed.

8. A closed drainage system as claimed in claim 7 wherein a plurality of collection bags are provided, with a subsequent said collection bag being attached to said drainage device as soon as a used collection bag is removed from said drainage device, and wherein each said collection bag further includes a closure cap which is attached to said collection bag for said inlet of said collection bag.

9. A closed drainage system as claimed in claim 7 wherein each said collection bag further includes a skirt located around said inlet of said collection bag to help prevent contamination of said inlet and hence transfer of this contamination to said drainage device.

10. A closed drainage system as claimed in claim 9 wherein said outlet of said collection chamber includes an outer surface and wherein said skirt contacts the outer surface of said outlet of said collection chamber when said inlet of said collection bag is inserted in said outlet such that said skirt provides a cover and seal for said outlet to help prevent contamination of said outlet and subsequent contamination of said collection chamber.

11. A closed drainage system as claimed in claim 10 wherein said cap of each said collection bag contacts said respective skirt when said cap is engaged on said inlet to provide a seal around said inlet.

12. A closed drainage system as claimed in claim 11 wherein said collection bags are made of a transparent plastics material and further include collected liquid calibrations thereon.

* * * * *